(12) United States Patent
Toby et al.

(10) Patent No.: US 7,343,920 B2
(45) Date of Patent: Mar. 18, 2008

(54) CONNECTIVE TISSUE REPAIR SYSTEM

(76) Inventors: E. Bruce Toby, 11109 W. 124th St., Overland Park, KS (US) 66213; Randall J. Huebner, 18000 SW. Bany Rd., Beaverton, OR (US) 97007

( * ) Notice: Subject to any disclaimer, the term of this patent is extended or adjusted under 35 U.S.C. 154(b) by 814 days.

(21) Appl. No.: 10/325,703

(22) Filed: Dec. 20, 2002

(65) Prior Publication Data

US 2004/0122471 A1   Jun. 24, 2004

(51) Int. Cl.
   *A62B 19/00* (2006.01)
(52) U.S. Cl. .................. 128/898; 606/142; 606/219
(58) Field of Classification Search .. 227/175.1–182.1; 606/215, 216, 219, 139, 142, 144, 220; 128/898
   See application file for complete search history.

(56) References Cited

U.S. PATENT DOCUMENTS

| | | | |
|---|---|---|---|
| 2,075,508 A | 3/1937 | Davidson | |
| 2,199,025 A | 4/1940 | Conn | |
| 2,802,468 A | 8/1957 | Everett | |
| 3,079,608 A | 3/1963 | Babkin | |
| 3,123,077 A | 3/1964 | Alcamo | |
| 3,545,444 A | 12/1970 | Green | |
| 3,570,497 A | 3/1971 | Lemole | |
| 3,735,762 A | 5/1973 | Bryan et al. | |
| 3,875,946 A | 4/1975 | Duncan | |
| 3,890,975 A | 6/1975 | McGregor | |
| 3,976,079 A | 8/1976 | Samuels et al. | |
| 3,981,307 A | 9/1976 | Borysko | |
| 4,086,926 A * | 5/1978 | Green et al. | 606/143 |
| 4,111,206 A * | 9/1978 | Vishnevsky et al. | 227/176.1 |
| 4,196,836 A | 4/1980 | Becht | |
| 4,344,193 A | 8/1982 | Kenny | |
| 4,349,028 A * | 9/1982 | Green | 606/143 |
| 4,359,053 A | 11/1982 | Benjamin | |
| D271,332 S | 11/1983 | Green et al. | |
| 4,506,670 A | 3/1985 | Crossley | |
| 4,549,545 A | 10/1985 | Levy | |
| 4,606,344 A | 8/1986 | Di Giovanni | |
| 4,633,874 A * | 1/1987 | Chow et al. | 227/176.1 |
| 4,635,637 A | 1/1987 | Schreiber | |
| 4,649,920 A | 3/1987 | Rhum | |
| 4,665,916 A | 5/1987 | Green | |
| 4,712,550 A | 12/1987 | Sinnett | |
| 4,741,330 A | 5/1988 | Hayhurst | |

(Continued)

FOREIGN PATENT DOCUMENTS

EP   0 314 412   10/1993

(Continued)

OTHER PUBLICATIONS

Arthroscopic Meniscal Repair, Clancy, Jr. et al., *Orthopedics*, vol. 6, No. 9, pp. 1125-1129, Sep. 1983.

(Continued)

*Primary Examiner*—Michael J. Hayes
*Assistant Examiner*—Michael G. Mendoza
(74) *Attorney, Agent, or Firm*—Kolisch Hartwell, PC (57) ABSTRACT

Systems, including apparatus and methods, for repairing injured connective tissue. These systems may include, among others, a surgical stapler and staples for repairing partially or completely severed tendons and/or ligaments.

27 Claims, 5 Drawing Sheets

U.S. PATENT DOCUMENTS

| | | |
|---|---|---|
| 4,781,190 A | 11/1988 | Lee |
| 4,790,303 A | 12/1988 | Steffee |
| 4,858,603 A | 8/1989 | Clemow et al. |
| 4,869,242 A | 9/1989 | Galluzzo |
| 4,873,976 A | 10/1989 | Schreiber |
| 4,875,479 A | 10/1989 | Belykh et al. |
| 4,895,148 A | 1/1990 | Bays et al. |
| 4,901,712 A | 2/1990 | Voegell et al. |
| 4,926,860 A | 5/1990 | Stice et al. |
| 4,950,285 A | 8/1990 | Wilk |
| 4,976,715 A | 12/1990 | Bays et al. |
| 4,981,149 A | 1/1991 | Yoon et al. |
| 4,997,436 A | 3/1991 | Oberlander |
| 5,002,562 A | 3/1991 | Oberlander |
| 5,053,047 A | 10/1991 | Yoon |
| 5,059,206 A | 10/1991 | Winters |
| 5,061,283 A | 10/1991 | Silvestrini |
| 5,102,421 A | 4/1992 | Anspach, Jr. |
| 5,154,189 A | 10/1992 | Oberlander |
| 5,171,250 A | 12/1992 | Yoon |
| 5,209,756 A | 5/1993 | Seedhom et al. |
| 5,211,647 A | 5/1993 | Schmieding |
| 5,236,440 A | 8/1993 | Hlavacek |
| 5,242,457 A | 9/1993 | Akopov et al. |
| 5,269,783 A | 12/1993 | Sander |
| 5,374,268 A | 12/1994 | Sander |
| 5,392,978 A | 2/1995 | Velez et al. |
| 5,398,861 A | 3/1995 | Green |
| 5,425,766 A | 6/1995 | Bowald |
| 5,431,669 A | 7/1995 | Thompson et al. |
| 5,458,636 A | 10/1995 | Brancato |
| 5,484,095 A | 1/1996 | Green et al. |
| 5,500,000 A | 3/1996 | Feagin et al. |
| 5,514,181 A | 5/1996 | Light et al. |
| 5,527,342 A | 6/1996 | Pietrzak et al. |
| 5,547,474 A | 8/1996 | Kloeckl et al. |
| 5,569,252 A | 10/1996 | Justin et al. |
| 5,639,008 A | 6/1997 | Gallagher et al. |
| 5,665,109 A | 9/1997 | Yoon |
| 5,674,247 A | 10/1997 | Sohn |
| 5,722,982 A | 3/1998 | Ferreira et al. |
| 5,723,008 A | 3/1998 | Gordon |
| 5,725,554 A | 3/1998 | Simon et al. |
| 5,738,474 A | 4/1998 | Blewett |
| 5,741,251 A | 4/1998 | Benoist |
| 5,800,544 A | 9/1998 | Demopulos et al. |
| 5,868,789 A | 2/1999 | Huebner |
| 5,879,371 A | 3/1999 | Gardiner et al. |
| 5,893,855 A | 4/1999 | Jacobs |
| 5,902,319 A | 5/1999 | Daley |
| 5,911,352 A | 6/1999 | Racenet et al. |
| 5,916,224 A | 6/1999 | Esplin |
| 5,925,078 A | 7/1999 | Anderson |
| 5,928,251 A | 7/1999 | Aranyi et al. |
| 5,961,521 A | 10/1999 | Roger |
| 5,972,024 A | 10/1999 | Northrup, III et al. |
| 6,036,701 A | 3/2000 | Rosenman |
| 6,080,192 A | 6/2000 | Demopulos et al. |
| 6,102,947 A | 8/2000 | Gordon |
| 6,106,556 A | 8/2000 | Demopulos et al. |
| 6,113,611 A | 9/2000 | Allen et al. |
| 6,190,401 B1 | 2/2001 | Green et al. |
| 6,277,131 B1 | 8/2001 | Kalikow |
| 6,306,149 B1 | 10/2001 | Meade |
| 6,322,571 B1 | 11/2001 | Adams |
| 6,322,580 B1 | 11/2001 | Kanner |
| 6,447,516 B1 | 9/2002 | Bonutti |
| 6,726,705 B2 * | 4/2004 | Peterson et al. ............ 606/216 |

FOREIGN PATENT DOCUMENTS

| | | |
|---|---|---|
| EP | 0 390 613 | 8/1994 |
| WO | WO86/03396 | 6/1986 |
| WO | WO87/01270 | 3/1987 |

OTHER PUBLICATIONS

Arthroscopic Repair of Meniscus Tears, Henning, *Orthopedics*, vol. 6, No. 9, pp. 1130-1132, Sep. 1983.

A Technique of Arthroscopic Meniscoplasty, DiStefano et al., *Orthopedics*, vol. 6, No. 9, pp. 1135-1140, Sep. 1983.

*A Needle Guided Resorbable Staple for Arthroscopic Meniscal Repair*, Justin, University of Central Florida, pp. 127-130, undated.

* cited by examiner

CONNECTIVE TISSUE REPAIR SYSTEM

FIELD OF THE INVENTION

The invention relates to systems for repairing injured connective tissue, including, more particularly, a surgical stapler and staples for repairing partially or completely severed tendons and/or ligaments.

BACKGROUND

Tendons and ligaments are two of several types of connective tissues found in vertebrate organisms. Tendons are bands of fibrous tissue that connect muscles to bones. Ligaments are bands or sheets of fibrous tissue that connect bones or cartilages to one another at a joint or that support an organ. Tendons are essential to joint movement, being present throughout the body, and being particularly numerous throughout the forearm, hand, ankle, and foot.

Tendons and ligaments are susceptible to a variety of injuries, ranging from tears to complete severance. For example, because they usually are superficial in location, tendons often are injured by penetrating injuries, such as lacerations.

Unfortunately, tendon and ligament injuries may be difficult to repair, for a variety of reasons. For example, the ends of torn connective tissue tend to pull apart significantly after injury, making it unlikely that the injury will heal without surgery to hold the torn ends together. For this reason, tendons often are repaired by pulling the ends of the severed tendon into contact and then stitching them together. Unfortunately, as the repaired tendon heals, the point of reattachment may exhibit adhesion, that is, the abnormal development of new tissue joining the tendon to the surrounding tendon sheath. Adhesion may be reduced by early passive or active movement of the affected joint. Yet, damaged tendons require more force to move after surgery than undamaged tendons, putting additional stress on the sutures used to repair the tendon, frequently resulting in rupture of the tendon before it can heal. Surgeons therefore are encouraged to utilize increasingly complex multistrand repairs, resulting in increased operative time, increased foreign body suture material, and increased handling and manipulation of the tendon. While such procedures enhance the strength of the repair, they also enhance the likelihood of adhesion by the presence of the suture material and/or multiple or large suture knots, and by any rough handling of the involved tissues.

Thus, there is a need for a new system for repairing connective tissue, such as tendons and ligaments, that allows their quick and reproducible repair, while leaving the repaired tissue sufficiently strong to permit early range of motion of the involved joint.

SUMMARY OF THE INVENTION

The invention provides systems, including apparatus and methods, for repairing injured connective tissue. These systems may include, among others, a surgical stapler and staples for repairing partially or completely severed tendons and/or ligaments.

DETAILED DESCRIPTION

The invention provides systems, including apparatus and methods, for repairing injured connective tissue. These apparatus may include, among others, a surgical stapler and staples for repairing partially or completely severed tendons and/or ligaments. The methods may include, among others, methods of using a surgical stapler and/or staples for effecting such repair. Exemplary apparatus and methods are described below, including (I) staplers, (II) staples, (III) methods of use, (IV) staple configurations, and (V) additional considerations.

I. Staplers

FIGS. 1-4 show exemplary connective tissue staplers, for repairing partially or completely severed tendons and ligaments, in accordance with aspects of the invention. The stapler may include one or more of the following components, among others: (1) a staple driver, configured to advance or drive the legs of a surgical staple through an injured band of connective tissue, (2) an anvil, configured to deflect at least a portion of the legs of the surgical staple as they emerge from the band of connective tissue, back into the band and/or around the exterior of the band, (3) a trigger, operatively connected to the staple driver, configured so that the staple may be advanced by actuating the trigger, (4) a handle, configured for holding or grasping during stapling, (5) a housing, configured to enclose and/or support the staple driver and/or other components of the stapler, and/or (6) a clamp, configured to hold the connective tissue for stapling.

Figure 1:
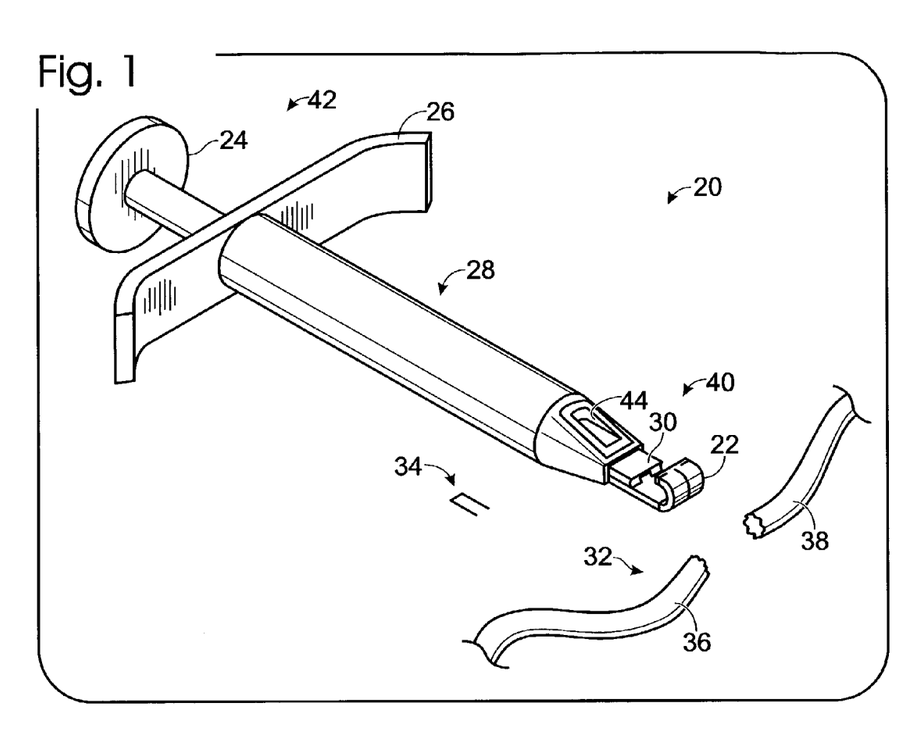
FIG. 1 is an isometric view of a connective tissue repair apparatus, in accordance with aspects of the invention.

FIG. 1 shows an external view of an exemplary connective tissue repair apparatus (or stapler) 20. Stapler 20 may include a staple driver (shown below), an anvil 22, and a trigger 24. Stapler 20 further may include a handle 26, a housing 28, and a clamp 30. Stapler 20 may be actuated by moving or urging trigger 24 and handle 26 toward one another, for example, by pushing trigger 24 while holding handle 26. In particular, in this embodiment, a user preferably pushes the trigger with a thumb or palm, while holding the handle with the fingers.

The anvil may be used to support a band or sheet of injured connective tissue 32 for the insertion of a surgical staple 34 by the apparatus. The injured connective tissue may be a tendon, a ligament, and/or any other suitable type of connective tissue. The term "injured," as used herein, includes any damage to the connective tissue, for example, cuts, tears, lacerations, and/or other form(s) of hurt. In some cases, the injured connective tissue may be partially or completely severed. If completely severed, the connective tissue may include first 36 and second 38 ends that must be rejoined.

The housing may be used to enclose and/or support components of the apparatus. Here, housing 28 substantially encloses the staple driver, while supporting (directly and/or indirectly) anvil 22, trigger 24, and handle 26. In this way, the housing may protect portions of the apparatus, while maintaining the proper spatial and/or functional relationships between the same and/or other portions of the apparatus. For example, the trigger and/or handle may be displaced physically from the anvil, so that the stapler may be held and/or actuated without interfering with the placement of connective tissue in the anvil and/or the interaction of the tissue with the staples. Here, the stapler is elongate, with the anvil positioned at a first (nose) end 40, and the trigger and handle positioned generally at an opposite (butt) end 42. The housing may include additional features, as desired or warranted, such as a staple port 44 for adding and/or storing staples, prior to use.

Figure 2:
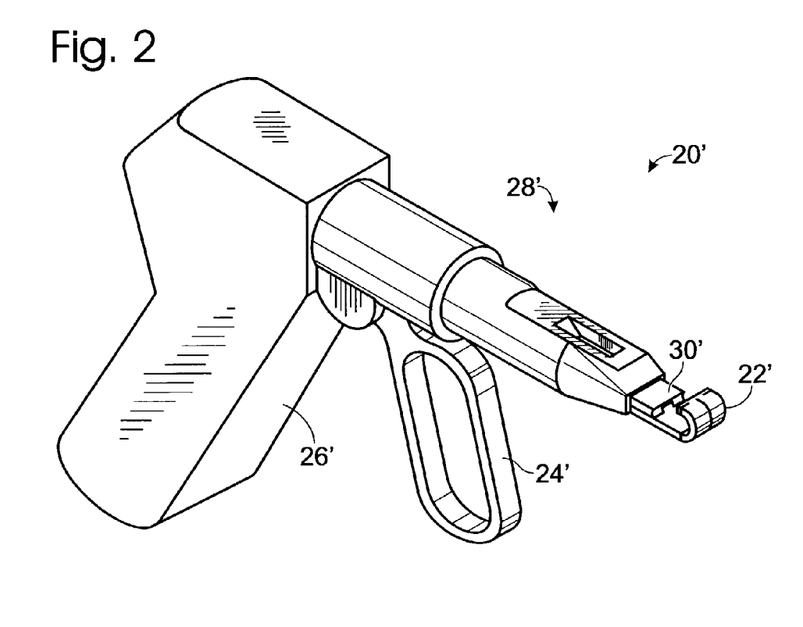
FIG. 2 is an isometric view of an alternative connective tissue repair apparatus, in accordance with aspects of the invention.

FIG. 2 shows an external view of another exemplary connective repair apparatus (or stapler) 20', with an alternative trigger/handle mechanism. Stapler 20' may include a staple driver (shown below), an anvil 22', and a trigger 24'. Stapler 20' further may include a handle 26', a housing 28', and a clamp 30'. Stapler 20' may be actuated, like stapler 20, by moving or urging trigger 24' and handle 26' toward one another. However, in this embodiment, a user preferably holds the handle using selected fingers and thumb, and pulls the trigger using a remaining finger.

Figures 3, 4:
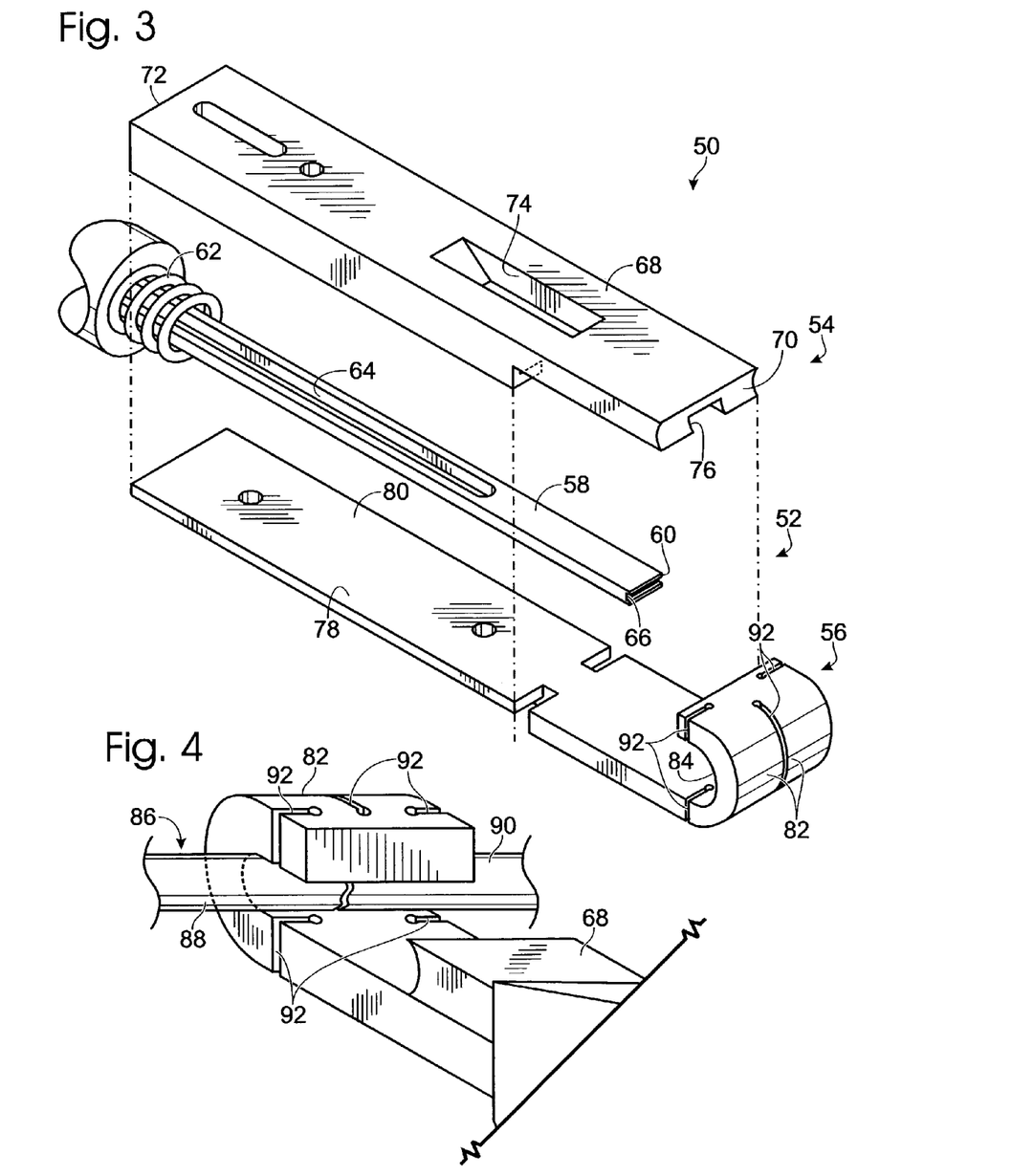
FIG. 3 is an exploded isometric view of a portion of the nose section of the connective tissue repair apparatus of FIG. 1.
FIG. 4 is a view of the nose of the connective tissue repair apparatus of FIG. 1, shown cradling an injured band of connective tissue.

FIGS. 3 and 4 show portions of an exemplary stapler (such as the staplers of FIGS. 1 and 2) that are involved in the delivery and shaping of staples. These portions, which are primarily from the nose end 50 of the stapler, include, among others, a staple driver 52, a clamp 54, and an anvil 56.

The staple driver may include an elongate driver body 58 having a driver face 60 at a first (nose-directed) end, a spring 62 near a second (butt-directed) end, and an elongate slot 64 disposed at least partially in between. The driver face may be configured to hold a surgical staple in an orientation suitable for its insertion into connective tissue when the apparatus is operated, typically by including one or more concave features on the driver face that are complementary to the surgical staple being utilized. For example, the staple driver face may include a lateral groove 66 sized so that a bridging portion of the surgical staple (shown below) may be at least partially inserted into the groove. The staple driver may be operatively connected to a trigger mechanism, such that activating the trigger advances the staple driver, and thus the loaded surgical staple, toward the anvil.

The clamp may include an elongate clamp body 68, with a clamp face 70 at a first (nose-directed) end, a spring-engaging face 72 near a second (butt-directed) end, a staple opening 74 for loading staples, and a guide channel 76 for receiving a staple driver. Staple opening 74 may align with a staple port in the stapler housing (see, e.g., FIG. 1), so that staples may be inserted (manually or automatically) into the stapler in advance of the staple driver face. Guide channel 76 may be configured to receive and guide the stapler driver between (1) a loading position, biased toward the butt end of the stapler, where the driver may receive a staple, and (2) a stapling position, biased toward the nose end of the stapler, where the driver may clamp the injured connective tissue and/or deliver the staple. The guide channel may form a longitudinal groove, as shown, into which the staple driver may fit, bounded on three sides by substantially planar faces of the clamp body, and bounded on a fourth side by an extended portion 78 of the anvil. The clamp body may include a projection on its underside that mates with slot 64 in staple driver body 58, allowing the staple driver to slide along the clamp body within limits defined by the length of slot 64.

The anvil may include a elongate anvil body 80, with an extended portion 78 toward a first (butt-directed) end, and a staple-shaping portion 82 near a second (nose-directed) end. The staple-shaping portion may include a concave channel 84, configured so that it can cup a band of injured connective tissue 86 in an appropriate position and orientation to facilitate the insertion of one or more staples into the injured connective tissue, typically so that the site of injury is bridged by the staple. In particular, as shown in FIG. 4, where the connective tissue is severed, the concave channel may substantially support the first 88 and second 90 severed ends of the connective tissue in abutment, that is, in direct contact with little or no gap between the first and second ends. The concave channel may act in concert with clamp face 70 of clamp 54. The anvil further may include one or more slots 92 and/or other features or openings to facilitate the use of sutures in the repair of the injured connective tissue.

The stapler (and components thereof) may be sized in accordance with the size and/or type of connective tissue under repair. For example, for typical tendon repairs, the length of the entire repair apparatus may range between about 80 mm and about 120 mm, and the width of the anvil may range between about 7 mm and about 14 mm. (Exemplary flexor tendons may have widths of about 4.7±1.2 mm or 4.3±0.2 mm, and heights of about 3.0±0.4 mm or 3.0±0.7 mm, among others.) Generally, relatively larger apparatus will facilitate the repair of larger connective tissues, whereas relatively smaller or more delicate apparatus will facilitate the repair of smaller connective tissues (e.g., via microsurgery).

The stapler (and components thereof) may be made of any suitable material(s), including metal, plastic, and/or the like. These materials may be capable of sterilization, for example, by autoclaving and/or irradiating, especially for reusable staplers. The materials may be selected to reduce or eliminate damage to connective tissue and/or surrounding tissue, for example, by being smooth and/or nonimmunogenic. The stapler (or portions thereof) may be colored or otherwise marked to distinguish it from other (size) staplers and/or from other surgical instruments.

II. Staples

Figure 5:
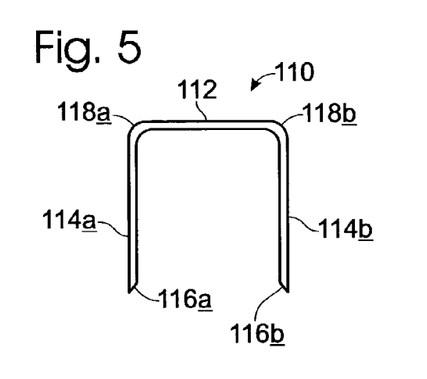
FIG. 5 is a front elevation view of a surgical staple, in accordance with aspects of the invention.
Figure 6:
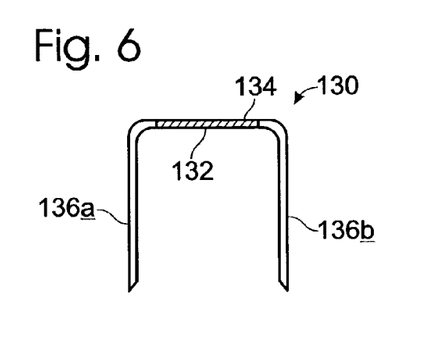
FIG. 6 is a front elevation view of an alternative surgical staple, in accordance with aspects of the invention.
Figure 7:
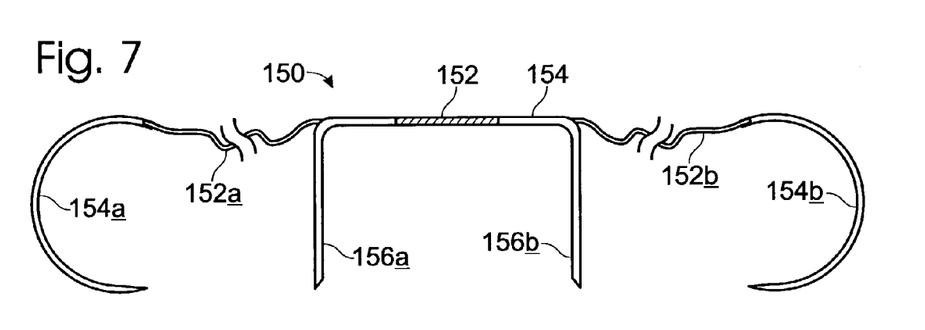
FIG. 7 is a front elevation view of another alternative surgical staple, with attached sutures, in accordance with aspects of the invention.

FIGS. 5-7 show exemplary staples for use in repairing connective tissue, in accordance with aspects of the invention. These staples generally may be used for the repair of any suitable tissue, preferably connective tissue, and preferably in conjunction with a repair apparatus, such as the connective tissue repair apparatus described herein.

FIG. 5 shows an exemplary surgical staple 110. This staple includes an elongate bridge portion 112 from which project (or depend) first and second legs 114a,b having ends or tips 116a,b, respectively. These ends or tips may be shaped or sharpened to facilitate their passage through tissue. Generally, although not necessarily, elongated bridge portion 112 and depending legs 114a,b lie in the same plane, with all formed integrally from a single piece of wire and/or other thin elongate material. The bridge portion and legs may be separated or distinguished by bends 118a,b. (Staples generally, though not necessarily, may be prebent to form the bridge portion and legs prior to their being loaded into a stapler.) The staple may be flexible enough to be deformed readily upon being driven into the anvil of the apparatus, while rigid enough to hold whatever shape is applied to the staple by the anvil. The cross-section of the staple material may have any suitable shape, such as circular and/or rectangular, with the shape and/or cross-sectional area remaining constant or varying over part or all of the staple.

FIG. 6 shows an alternative surgical staple 130. The alternative staple may incorporate one or more flexible sections 132, typically, although not necessarily, in the elongate bridge 134 of the staple, with legs 136a, b retaining sufficient rigidity to be shaped by the anvil. The flexible section may derive its flexibility by any suitable mechanism, for example, by including suture material, nitinol, and so on. The use of staples that incorporate flexible sections may increase the flexibility of repaired regions of connective tissue, relative to regions repaired with staples that are more rigid. Thus, flexible staples may facilitate the movement of repaired connective tissue through narrow anatomical passages, for example, the flexor tendon pulleys and sheaths in the hand, with substantially less adhesion and irritation. The flexible section or sections may be joined or secured onto the legs of the staple using any suitable mechanism, including swaging, crimping, gluing, and the like. For example, suture material may be inserted into a hollow needle, whereupon the sleeve may be crimped securely around the suture, so that the needle forms a leg of the resulting staple.

FIG. 7 shows yet another alternative surgical staple 150. Staple 150 optionally includes a flexible section 152 in the elongate bridge 154 between legs 156a, b of the staple. In addition, staple 150 includes two lengths of flexible suture or wire 152a, b and 53, each attached to a different staple leg near the elongate bridge. Sutures 152a, b and 53 terminate in needles, 154a, b, respectively, so that once staple 150 has been inserted into a band of connective tissue, the staple may be sutured in place, further reinforcing the repair to the connective tissue. The suture or wire generally comprises any material suitable for stitching around and/or through tissue, including standard suture, flexible wire, and so on. The needles generally comprise any surgical needles suitable for stitching around and/or through tissue, narrow or wide gauge, curved or straight, and so on, as dictated or warranted by the application.

The surgical staples provided by the invention generally may have any suitable design (e.g., size, shape, and/or material) effective for stabilizing and/or repairing an injury to a band of connective tissue. Thus, the surgical staples may include, independently, one or more flexible segments and/or one or more additional sutures, which may or may not include preattached needles. For example, the surgical staple may include only one length of additional suture attached to one leg of the staple. The staples may be sized to correspond, according to any suitable metric, to the size of the connective tissue to be repaired, for example, with a bridge portion long enough to span the tear or severance, possibly including any fraying, and with legs long enough to wrap at least partially around and/or penetrate at least partially into the connective tissue. For example, the length of the bridge portion may range between about 1 mm and about 20 mm, or between about 5 mm and about 15 mm, or be about 8 mm, 10 mm, or 12 mm, among others. Similarly, the length of the legs may range between about 1 mm and about 20 mm, or between about 5 mm and about 10 mm, or be about 7.5 mm, among others. Finally, the diameter of the bridge portion and/or legs may range between about 0.01 mm and about 2 mm, or between about 0.1 mm and about 1 mm, or be about 0.5 mm, among others. The staples may be shaped before use to fit within and/or to be bent by a stapler, and they may be shaped after use to support a particular connective tissue for healing (see, e.g., Section IV below). The staples may be formed of any suitable material(s), particularly biocompatible material(s), including stainless steel, titanium, suture, and/or resorbable material, among others.

III. Methods of Use

Figure 8A:
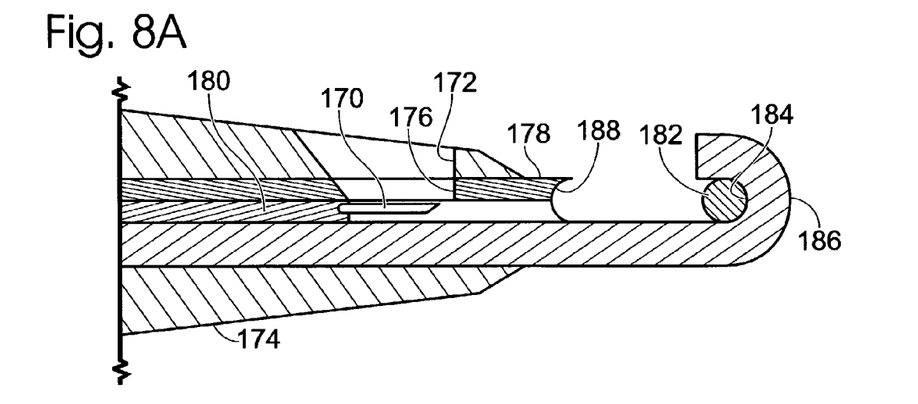
FIG. 8A is a cross-sectional side view of the nose of the connective tissue repair apparatus of FIG. 1, shown cradling an injured band of connective tissue.
Figure 8B:
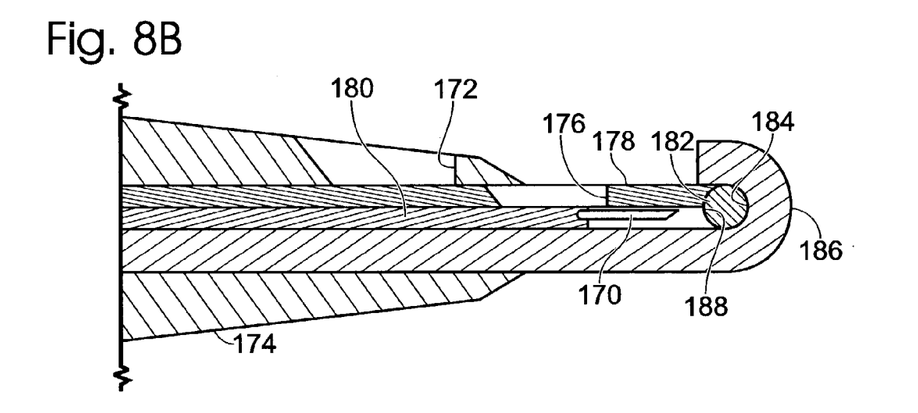
FIG. 8B is a cross-sectional side view of the nose of the connective tissue repair apparatus of FIG. 1, shown cradling an injured band of connective tissue, with the clamp body advanced to hold the connective tissue firmly.
Figure 8C:
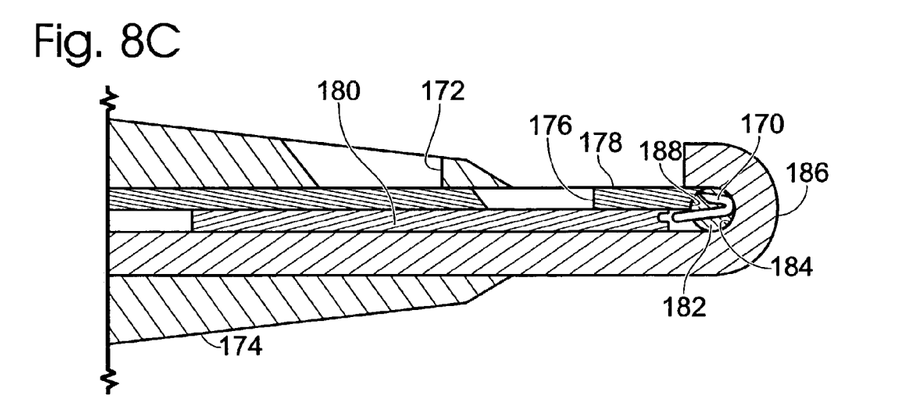
FIG. 8C is a cross-sectional side view of the nose of the connective tissue repair apparatus of FIG. 1, shown cradling an injured band of connective tissue, after the surgical staple has been driven through the connective tissue.

FIGS. 8A-C, viewed together with FIGS. 1, 3, and 4, show an exemplary three-stage method for operating repair apparatus 20 (or 20'). This exemplary method is included for illustration and is not intended to limit or define the entire scope of the invention. The connective tissue repair apparatus provided by the invention generally may be operated in any suitable or desired manner.

Stage 1 of the exemplary method comprises properly positioning the connective tissue in the stapler. First, the stapler is loaded (if not already loaded) by inserting a staple 170 through a staple port 172 in stapler housing 174 and a stapler opening 176 in clamp body 178 so that the staple is positioned in front of staple driver 180. Next, a band or other piece of connective tissue 182 is placed in concave channel 184 of anvil 186, and the trigger of the apparatus is depressed toward the handle, urging staple driver 180, loaded staple 170, and the spring (see 62 in FIG. 3) toward the anvil (since the trigger mechanism is coupled to the staple driver); see FIG. 8A. The spring contacts the proximal end (see 72 in FIG. 3) of clamp body 178, advancing a clamp face 188 toward the anvil. Clamp face 188 may include a concave surface that generally is complementary to concave channel 184 of the anvil, so that the clamp face and concave channel, when in proximity, define a volume within which the injured connective tissue may be supported, aligned, and partially compressed, in anticipation of the insertion of the surgical staple. If the trigger is depressed further, the staple driver will continue to urge the clamp body toward the anvil, until eventually the clamp body reaches a point where it is prevented from advancing further, generally by contact with the anvil; see FIG. 8B. The clamp body preferably is stopped before it advances to a point where it would overly compress or crush the connective tissue, typically before it would compress the tissue to less than about 75% of its normal height. The injured band of connective tissue, at this point, should be clamped securely between anvil 186 and clamp face 188, substantially completing the first stage of the stapling process.

Stage 2 of the exemplary method comprises stapling the connective tissue to effect the repair. This stage is initiated by continuing to squeeze the trigger beyond the point at which the connected tissue is clamped securely. This causes staple driver 180 to advance further within the barrel of the apparatus, compressing the spring against the proximal end of clamp body 178, while allowing surgical staple 170 to continue to advance toward the connective tissue. Depressing the trigger further advances the staple driver through the guide channel (see 76 in FIG. 3) within clamp body 178, such that the tips of the surgical staple begin to protrude from an opening in clamp face 188 defined by the guide channel. The tips of the surgical staple then may be driven into the connective tissue; see FIG. 8C. The interior surface of channel 184 of anvil 186 may be configured so that the tips, and therefore the legs, of the staple are deflected and/or deformed as they emerge from the connective tissue after penetrating the width of the connective tissue, creating a desired staple configuration. In particular, the interior surface of the anvil may include grooves, ridges, and/or other features that direct the tips of the staple in the desired direction(s) as the staple is pushed into the anvil.

Stage 3 of the exemplary method comprises release and removal of the repaired connective tissue. After the tissue has been stapled, the trigger may be released, withdrawing the staple driver reciprocally through the guide channel, and away from the anvil and connective tissue. This releases tension applied by the spring, so that clamp face 188 no longer is urged against the anvil, although the clamp body may not retract until the projection on the underside of clamp body 178 contacts the distal end of the elongate slot (see 64 in FIG. 3) in staple driver 180. The repaired connective tissue then may be released from the apparatus, as or after the clamp body retracts.

IV. Staple Configurations

Figure 9:
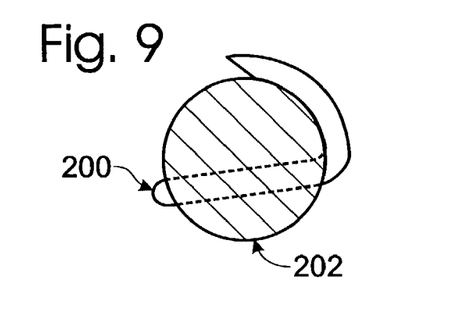
FIG. 9 is a cross-sectional view of a repaired band of connective tissue, taken along a long axis of the connective tissue, showing a surgical staple configuration.
Figure 10:
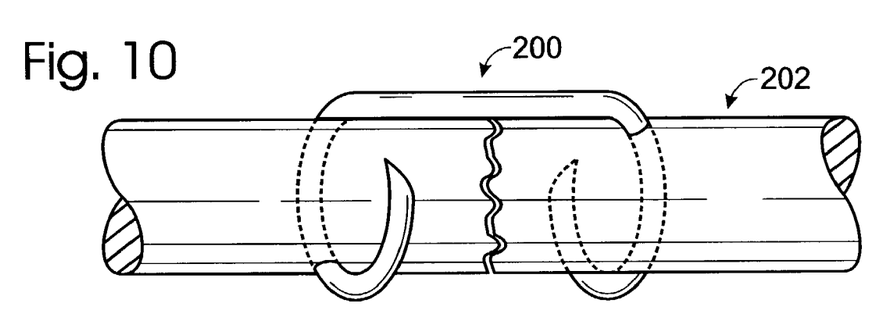
FIG. 10 is a side view of a repaired band of connective tissue, taken along a long axis of the connective tissue, showing an alternative surgical staple configuration.
Figure 11:
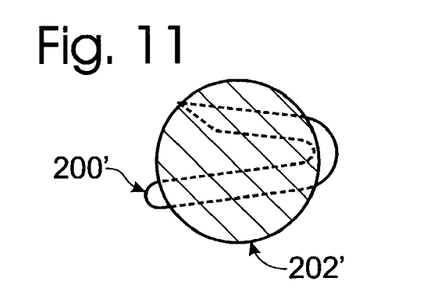
FIG. 11 is a cross-sectional view of a repaired band of connective tissue, showing another alternative surgical staple configuration.

FIGS. 9-11 show exemplary staple configurations. These configurations preferably are determined by the anvil, during stapling, as described above. However, in some embodiments, the configuration may be modified (or even established) after stapling, for example, by additional bending. These exemplary configurations are included for illustration and are not intended to limit or define the entire scope of the invention.

The staples generally may adopt and/or be formed into any configuration capable of and/or adapted to support the injured connective tissue for healing. Exemplary configurations may be two-dimensional (planar) or three-dimensional, and straight and/or curved. The long axis and legs of the staple independently may be aligned with, or offset from, the long axis of the connective tissue. For example, the long axis of the staple may be aligned with the connective tissue, with the legs offset between about 15 and about 45 degrees. Preferred staple configurations reduce the likelihood that the staple will loosen or pull out of the connective tissue, while enhancing healing. These configurations may additionally or alternatively bias the ends of the connective tissue toward one another, potentially enhancing repair. These configurations also may have relatively low surface profiles, to facilitate passage of the stapled tissue through constriction sites such as pulleys and/or sheaths.

FIGS. 9 and 10 show two related exemplary configurations, in which the interior surface of the anvil deflects and directs the legs of the surgical staple 200 into a configuration such that at least one leg of the staple is curled around the outer surface of the connective tissue 202. If two legs of the staple are so curled, each leg may curl in the same direction, or, as shown in FIG. 10, each may curl in a different direction FIG. 11 shows another exemplary configuration, in which, as the tips of the surgical staple 200' exit the connective tissue 202', the anvil deflects and directs the staple tips back into the connective tissue, for one or both legs of the staple. This configuration, in which the staple penetrates the connective tissue more than once, may provide additional strength to the tissue repair. This configuration also may reduce irritation of the tissues surrounding the repair site, as it exposes a reduced amount of foreign material to that tissue. For example, if the connective tissue is a tendon, the reduced exposure to the staple materials may reduce irritation to the tendon sheath, and therefore reduce tendon adhesion during recovery.

V. Additional Considerations

Staples may be used alone or together with other mechanisms, as necessary or desired to stabilize and repair injuries to connective tissue. For example, in some cases, tissue repair adequately may be effected by application of a surgical staple alone, so that additional medical procedures are unnecessary. This more likely will be true for simpler injuries, such as partial rather than complete severance. In other cases, tissue repair may be enhanced by inserting one or more additional staples into the connective tissue bridging the site of the injury. The application of additional staples may be improved by applying additional staples at distinct and nonintersecting angles to each other. Additionally, or in the alternative, tissue repair may be enhanced by applying one or more stitches or sutures across the site of the injury, increasing the strength of the repair. Sutures generally may be applied before the injured tissue is placed in the apparatus, while the tissue resides in the apparatus, and/or after the tissue is removed from the apparatus. Preferably, the stapler and/or staple are configured to facilitate suturing. Thus, the stapler anvil may include one or more slots or ports (see, e.g., slots 82 in FIGS. 3 and 4) to facilitate the application of one or more sutures to the injured connective tissue. These sutures may be applied using materials and methods known in the art. Alternatively, or in addition, the surgical staple itself may include a suture and needle (see, e.g., FIG. 7) to facilitate application of sutures across the site of the injury, preferably utilizing slots provided in the anvil.

The repair apparatus may be configured, in some embodiments, for a single use, for example, using one or more preloaded staples. These embodiments may be prepackaged in a sterile wrapper. Thus, as needed, the repair apparatus could be removed from the sterile wrapper, used to deploy a staple into the injured connective tissue, and then discarded.

The repair apparatus also may be configured, in other embodiments, for reloading additional staples, or different types of staples, for effecting multiple repairs, during the same or different surgical procedures. For example, the repair apparatus may include a staple port for receiving new staples, directly or via a clip or cassette that houses the staples, so that a plurality of surgical staples may be applied before the repair apparatus must be refilled with additional staples. Alternatively, or in addition, the stapling apparatus may be configured to insert multiple staples into the connective tissue during a single stapling operation, typically at distinct angles.

The repair apparatus may be provided alone and/or as part of a surgical kit for connective tissue repair. The kit optionally may include additional supplies, such as surgical staples of one or more sizes or styles. The kit also may include additional tools and/or consumable surgical supplies that may be required for carrying out the connective tissue repair, substantially as described above, such as additional clamps and/or other surgical tools that may facilitate grasping and/or positioning the connective tissue that is being repaired.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A method of repairing an injured band of tendon and/or ligament, comprising:
   positioning first and second ends of an injured band of tendon and/or ligament against an anvil of a surgical stapler, such that the ends are aligned and abutted;
   applying at least one staple to the injured band of so that the staple engages both the first end and the second end of the injured band of; and
   removing the band of from the anvil,
   wherein the step of applying the at least one staple to the injured band of includes (1) a step of driving tips of the staple through the band of, and (2) a step of deflecting the tips of the staple against the anvil after they emerge from the band of.

2. The method of claim 1, wherein the staple includes an elongate bridge portion having opposite ends and a flexible region and also includes a first leg and a second leg depending from the ends of the elongate bridge portion, wherein the step of driving includes a step of disposing the first leg and the second leg in distinct end regions of the band of connective tissue such that the flexible region of the elongate bridge portion spans a site of injury in the band of connective tissue.

3. The method of claim 1, wherein the staple includes one or more suture segments attached to the staple, further comprising a step of suturing the staple to the band of using at least one of the suture segments attached to the staple.

4. The method of claim 3, wherein the at least one suture segment terminates in a needle, and wherein the step of suturing employs the needle.

5. The method of claim 1, the staple being applied by a stapler, further comprising:
   removing the stapler from a sterile package;
   performing the step of applying with the stapler such that exactly one staple is applied to the band of; and
   discarding the stapler.

6. The method of claim 1, wherein the step of applying includes a step of actuating a trigger that advances the staple, and wherein a connective tissue clamp is operatively connected to the trigger such that the step of actuating clamps the band of connective tissue between the anvil and the clamp.

7. The method of claim 1, wherein the step of positioning includes steps of receiving and orienting the injured band of with the anvil.

8. The method of claim 1, further comprising a step of directing a tip of the at least one staple, after the step of driving, (1) back into the injured band of (2) around the exterior of the injured band of, or (3) both.

9. The method of claim 1, wherein the steps of positioning, applying, and removing are performed on an injured tendon.

10. The method of claim 1, further comprising a step of selecting a cassette including the at least one staple and a plurality of additional staples.

11. A method of repairing an injured band of tendon and/or ligament, comprising:
    positioning first and second ends of an injured band of tendon and/or ligament against an anvil of a surgical stapler, such that the ends are aligned and abutted;
    applying at least one staple to the injured band of so that the staple engages both the first end and the second end of the injured band of; and
    removing the band of from the anvil,
    wherein the step of applying includes a step of actuating a trigger that advances the staple, and wherein a connective tissue clamp is operatively connected to the trigger such that the step of actuating clamps the band of between the anvil and the connective tissue clamp.

12. The method of claim 11, wherein the staple includes one or more suture segments attached to the staple, further comprising a step of suturing the staple to the band of using at least one of the suture segments attached to the staple.

13. The method of claim 12, wherein the at least one suture segment terminates in a needle, and wherein the step of suturing employs the needle.

14. The method of claim 11, wherein the step of positioning includes steps of receiving and orienting the injured band of with the anvil.

15. The method of claim 11, wherein the at least one staple has ends, and wherein the step of applying includes a step of penetrating through the injured band of with the ends of the at least one staple, further comprising a step of directing an end of the at least one staple, after the step of penetrating, (1) back into the injured band of, (2) around the exterior of the injured band of, or (3) both.

16. The method of claim 11, wherein the steps of positioning, applying, and removing are performed on an injured tendon.

17. The method of claim 11, further comprising a step of selecting a cassette including the at least one staple and a plurality of additional staples.

18. A method of repairing an injured band of tendon and/or ligament, comprising:
    positioning first and second ends of an injured band of tendon and/or ligament against an anvil of a surgical stapler, such that the ends are aligned and abutted;
    applying at least one staple to the injured band of so that the staple engages both the first end and the second end of the injured band of; and
    removing the band of from the anvil,
    wherein the at least one staple has ends, and wherein the step of applying includes a step of penetrating through the injured band of with the ends of the at least one staple, further comprising a step of directing an end of the at least one staple back into the injured band of after the step of penetrating.

19. A method of repairing an injured band of tendon and/or ligament, comprising:

positioning first and second ends of an injured band of tendon and/or ligament against an anvil of a surgical stapler, such that the ends are aligned and abutted;

applying at least one staple to the injured band of so that the staple engages both the first end and the second end of the injured band of; and removing the band of from the anvil, wherein the at least one staple has ends, and wherein the step of applying includes a step of penetrating through the injured band of with the ends of the at least one staple, further comprising a step of directing an end of the at least one staple around the exterior of the injured band of after the step of penetrating.

20. A method of repairing an injured band of tendon and/or ligament, comprising:

positioning first and second ends of an injured band of tendon and/or ligament against an anvil of a surgical stapler, such that the ends are aligned and abutted;

applying at least one staple to the injured band of so that the staple engages both the first end and the second end of the injured band of; and removing the band of from the anvil.

21. The method of claim 20, wherein the staple includes an elongate bridge portion having opposite ends and a flexible region and also includes a first leg and a second leg depending from the ends of the elongate bridge portion, and wherein the step of applying includes a step of disposing the first leg and the second leg in distinct end regions of the band of such that the flexible region of the elongate bridge portion spans a site of injury in the band of.

22. The method of claim 20, wherein the staple includes one or more suture segments attached to the staple, further comprising a step of suturing the staple to the band of using at least one of the suture segments attached to the staple.

23. The method of claim 22, wherein the at least one suture segment terminates in a needle, and wherein the step of suturing employs the needle.

24. The method of claim 20, the staple being applied by a stapler, further comprising:

removing the stapler from a sterile package;

performing the step of applying with the stapler such that exactly one staple is applied to the band of; and discarding the stapler.

25. The method of claim 20, wherein the step of positioning includes steps of receiving and orienting the injured band of with the anvil.

26. The method of claim 20, wherein the step of apply that at least one staple to the injured band includes a step of driving tips of the staple through the injured band, further comprising a step of directing the tips of the at least one staple, after the step of driving, (1) back into the injured band of, (2) around the exterior of the injured band of, or (3) both.

27. The method of claim 20, further comprising a step of selecting a cassette including the at least one staple and a plurality of additional staples.

* * * * *